United States Patent
Wittenberger et al.

(10) Patent No.: US 9,468,485 B2
(45) Date of Patent: Oct. 18, 2016

(54) REAL-TIME LESION FORMATION ASSESSMENT

(71) Applicant: MEDTRONIC CRYOCATH LP, Toronto (CA)

(72) Inventors: Dan Wittenberger, L'IleBizard (CA); Jean-Pierre Lalonde, Candiac (CA); Stephen A. Howard, Oakdale, MN (US)

(73) Assignee: Medtronic CryoCath LP, Toronto, Ontario (CA)

( * ) Notice: Subject to any disclaimer, the term of this patent is extended or adjusted under 35 U.S.C. 154(b) by 364 days.

(21) Appl. No.: 14/104,079

(22) Filed: Dec. 12, 2013

(65) Prior Publication Data

US 2015/0164570 A1   Jun. 18, 2015

(51) Int. Cl.
*A61B 18/02* (2006.01)
*A61B 18/00* (2006.01)

(52) U.S. Cl.
CPC ........ *A61B 18/02* (2013.01); *A61B 2018/0022* (2013.01); *A61B 2018/00375* (2013.01); *A61B 2018/00577* (2013.01); *A61B 2018/00791* (2013.01); *A61B 2018/00797* (2013.01); *A61B 2018/00839* (2013.01); *A61B 2018/0212* (2013.01); *A61B 2018/0293* (2013.01)

(58) Field of Classification Search
CPC .............. A61B 18/02; A61B 18/1492; A61B 2018/00577; A61B 2018/0212; A61B 2018/0022; A61B 2018/00351; A61B 2018/0262; A61B 2018/00023; A61B 2018/025; A61B 2018/00273; A61B 2018/00285
USPC .................................................... 606/20–26
See application file for complete search history.

(56) References Cited

U.S. PATENT DOCUMENTS

| 6,022,346 | A | 2/2000 | Panescu et al. |
| 6,423,057 | B1 | 7/2002 | He et al. |
| 6,514,249 | B1 * | 2/2003 | Maguire ................ A61B 18/00 606/37 |
| 6,517,533 | B1 * | 2/2003 | Swaminathan .... A61B 18/0218 600/3 |

(Continued)

FOREIGN PATENT DOCUMENTS

| EP | 0767630 A1 | 4/1997 |
| EP | 1906855 A2 | 4/2008 |

(Continued)

OTHER PUBLICATIONS

International Search Report and Written Opinion dated Feb. 12, 2015, for corresponding International Application No. PCT/CA2014/000853; International Filing Date: Nov. 28, 2014 consisting of 7-pages.

*Primary Examiner* — Michael Peffley
(74) *Attorney, Agent, or Firm* — Christopher & Weisberg, P.A.

(57) ABSTRACT

A method and system for creating permanent lesions in an area of target tissue, such as tissue at or proximate a junction between a pulmonary vein and the left atrium. The method may generally include positioning a medical device in contact with a pulmonary vein ostium, ablating the tissue, and recording a plurality of temperature measurements from one or more of three temperature sensors. The device may include an occlusion element in communication with a coolant source, a first sensor located distal of the occlusion element, a second sensor located proximal of the occlusion element, and a third sensor located in the occlusion element. One or more temperature measurements may be compared with each other to assess occlusion of the pulmonary vein, and/or may be compared with a set of reference temperatures to predict a real-time temperature within the target tissue.

22 Claims, 10 Drawing Sheets

(56) References Cited

U.S. PATENT DOCUMENTS

| | | | |
|---|---|---|---|
| 6,602,276 B2* | 8/2003 | Dobak, III | A61B 18/02 606/20 |
| 6,675,050 B2 | 1/2004 | Arndt et al. | |
| 6,702,811 B2* | 3/2004 | Stewart | A61B 18/1492 606/41 |
| 6,875,209 B2* | 4/2005 | Zvuloni | A61B 18/02 606/21 |
| 7,299,090 B2 | 11/2007 | Koch | |
| 7,318,004 B2 | 1/2008 | Butterfield | |
| 7,476,235 B2* | 1/2009 | Diederich | A61M 29/02 606/192 |
| 2003/0114843 A1* | 6/2003 | Lafontaine | A61B 18/02 606/21 |
| 2011/0077641 A1 | 3/2011 | Dunning | |
| 2011/0118727 A1 | 5/2011 | Fish et al. | |
| 2011/0125233 A1 | 5/2011 | Shen et al. | |
| 2012/0071746 A1 | 3/2012 | Vortman et al. | |
| 2012/0289855 A1 | 11/2012 | Bieberich et al. | |
| 2013/0158577 A1 | 6/2013 | Mahon et al. | |
| 2013/0238064 A1 | 9/2013 | Lafontaine | |

FOREIGN PATENT DOCUMENTS

| | | |
|---|---|---|
| WO | 9600043 A1 | 1/1996 |
| WO | 2007005963 A2 | 1/2007 |

* cited by examiner

REAL-TIME LESION FORMATION ASSESSMENT

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for the real-time assessment of lesions formed during a cryoablation procedure.

BACKGROUND OF THE INVENTION

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) and pulmonary vein antrum isolation (PVAI) are commonly used to treat atrial fibrillation. These procedures generally involve the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium or PV antrum. If a cryoballoon is used as the treatment element of the cryogenic device, the balloon is typically inflated using a fluid coolant, enabling an entire outer diameter of the balloon to create a circumferential lesion about the ostium and/or antrum of the PV to disrupt aberrant electrical signals exiting the PV.

The success of this procedure depends largely on the quality of the lesion(s) created during the procedure and whether the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

There are several ways in which lesion formation may be assessed, either during or after an ablation procedure. Such methods include imaging techniques, temperature measurement, temperature-time assessment, and cell-death models. However, each of these methods has its drawbacks. For example, standard imaging techniques may involve interrupting the ablation procedure to image the target tissue to determine if further ablation is required for sufficient lesion creation. This post-procedural medical imaging does not provide real-time lesion assessment and/or prevention of injury to non-target tissue. Further, measuring the temperature of target tissue during a procedure may be difficult or impossible, and methods that measure temperature within the cryoballoon to approximate the temperature of treated tissue may not take into account the tissue type and response to treatment, and can be very inaccurate. Likewise, temperature-time assessment methods may be based on a one-size-fits all model (for example, an Arrhenius-like equation) that does not take into account the type and depth of tissue, and may be subject to noise in the temperature data. Further, the cell-death models may not be very robust, may over- or under-estimate the effects an ablation procedure has on the target tissue, and different models may have to be used for different tissue.

It has been determined that real-time lesion formation assessment is one of the most important unmet needs for safety and efficacy of PVI using a cryoballoon catheter. None of the methods described above provides real-time temperature and occlusion feedback that can be used to assess lesion formation in real time.

Therefore, it is desirable to provide a cryoablation system and device that allows for the real-time lesion formation assessment by providing real-time temperature and occlusion feedback during a cryoablation procedure.

SUMMARY OF THE INVENTION

The present invention advantageously provides a method and system for creating permanent lesions in an area of target tissue, such as tissue at or proximate a junction between a pulmonary vein and the left atrium. In one embodiment, the method may generally include positioning a measuring device at least partially within the pulmonary vein, obtaining a plurality of temperature measurements, with the measuring device, of blood at a location within the pulmonary vein, and comparing the plurality of temperature measurements to a set of reference temperatures that correlate blood temperature to tissue temperature to provide a real-time temperature within a target tissue. The measuring device may include an occlusion element (for example, a cryoballoon) connectable to a source of coolant, circulation of coolant within the occlusion element causing the occlusion element to reach temperatures sufficient to ablate tissue, a first temperature sensor located distal of the occlusion element, and a second temperature sensor located within the occlusion element. The reference temperatures may be compiled using empirical data obtained from in vitro and/or in vivo experimentation. The target tissue may have a thickness, $d_3$, within which permanent cryoablation lesions may be created without damage to non-target tissue. The circulation of coolant within the occlusion element may be adjusted (for example, reduced or stopped) when a determined temperature within $d_3$ is substantially the same as a temperature, $T_{PL}$, at which permanent lesions are formed within the target tissue. For example, circulation of coolant within the occlusion element is adjusted when the determined temperature is within ±5° C. of $T_{PL}$. The measured temperatures may be correlated to the reference temperatures to determine a real-time temperature within the target tissue. The method may further include positioning the occlusion element at least partially within the pulmonary vein such that the first temperature sensor is disposed in the pulmonary vein and the second temperature sensor is disposed in a left atrium, obtaining a first plurality of temperature measurements with the first temperature sensor and obtaining a second plurality of temperature measurements with the second temperature sensor, and comparing the first and second pluralities of temperature measurements to determine whether the occlusion element is completely occluding the pulmonary vein. The measuring device may further include a third temperature sensor disposed within the occlusion element.

In another embodiment, the method may include positioning a medical device at least partially within a pulmonary vein ostium, the medical device including a cryoballoon, a first temperature sensor disposed in the pulmonary vein, a second temperature sensor disposed in a left atrium, and a third temperature sensor disposed within the cryoballoon, the cryoballoon being in fluid communication with a coolant source, obtaining a first plurality of temperature measurements with the first temperature sensor and obtaining a second plurality of temperature measurements with the second temperature sensor, comparing the first and second pluralities of temperature measurements to determine whether the cryoballoon is completely occluding the pulmonary vein, comparing the plurality of temperature measurements to a set of reference temperatures that correlate blood temperature to tissue temperature to provide a temperature within a thickness $d_3$ of a target tissue, thickness $d_3$ being a thickness within which permanent lesions may be created without damage to non-target tissue, and at least one of stopping and reducing a circulation of coolant within the cryoballoon when a determined temperature within $d_3$ is ±2° C. of a temperature at which permanent lesions are formed in the target tissue, $T_{PL}$. The measured temperatures may be correlated to the reference temperatures to determine a temperature within the target tissue.

In one embodiment, the system may include a medical device having an occlusion element coupled to a distal end of the medical device, a first temperature sensor coupled to the distal end of the medical device and located distal of the occlusion element, a second temperature sensor coupled to the distal end of the medical device and located proximal of the occlusion element, and a third temperature sensor located within the occlusion element. The system may further include a coolant source in fluid communication with the occlusion element and a computer programmable to execute an algorithm for comparing a first plurality of temperature measurements recorded by the first temperature sensor to a second plurality of temperature measurements recorded by the second temperature sensor to determine whether the occlusion element is occluding a pulmonary vein ostium and comparing the first plurality of temperature measurements to a set of reference temperatures that correlate blood temperature to tissue temperature to provide a temperature within the target tissue. The target tissue may have a thickness, $d_3$, within which permanent cryoablation lesions may be created without damage to non-target tissue. Circulation of coolant within the cryoballoon may be (for example, reduced or stopped) adjusted when a determined temperature within $d_3$ is ±2° C. of a temperature at which permanent lesions form in the target tissue, $T_{PL}$. The compute may further be programmed to generate an alert when a measurement of the first plurality of temperature measurements is within ±20° C. of a measurement of the second plurality of temperature measurements, and/or to compare the first plurality of measurements to a third plurality of temperature measurements recorded by the third temperature sensor.

BRIEF DESCRIPTION OF THE DRAWINGS

A more complete understanding of the present invention, and the attendant advantages and features thereof, will be more readily understood by reference to the following detailed description when considered in conjunction with the accompanying drawings, which may not be drawn to scale, wherein.

DETAILED DESCRIPTION OF THE INVENTION

Figure 1:
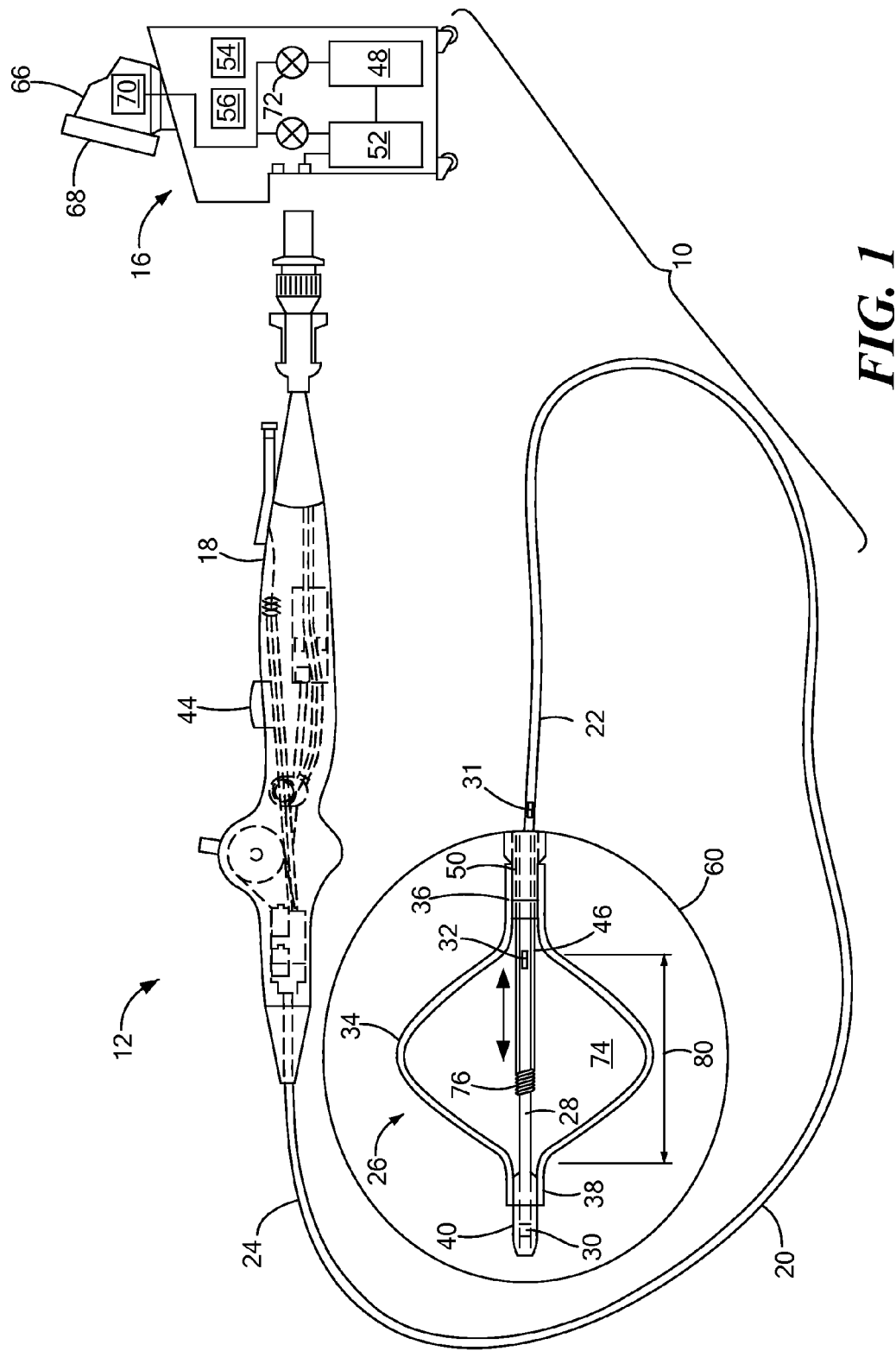
FIG. 1 shows an exemplary cryoablation system.

Referring now to FIG. 1, an exemplary cryoablation system is shown. The system 10 may generally include a treatment device, such as a cryotreatment catheter 12, for thermally treating an area of tissue, a mapping catheter 14 (shown in FIG. 2) for sensing and recording electrical signals from tissue (for example, cardiac tissue), and a console 16 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof.

Figure 2:
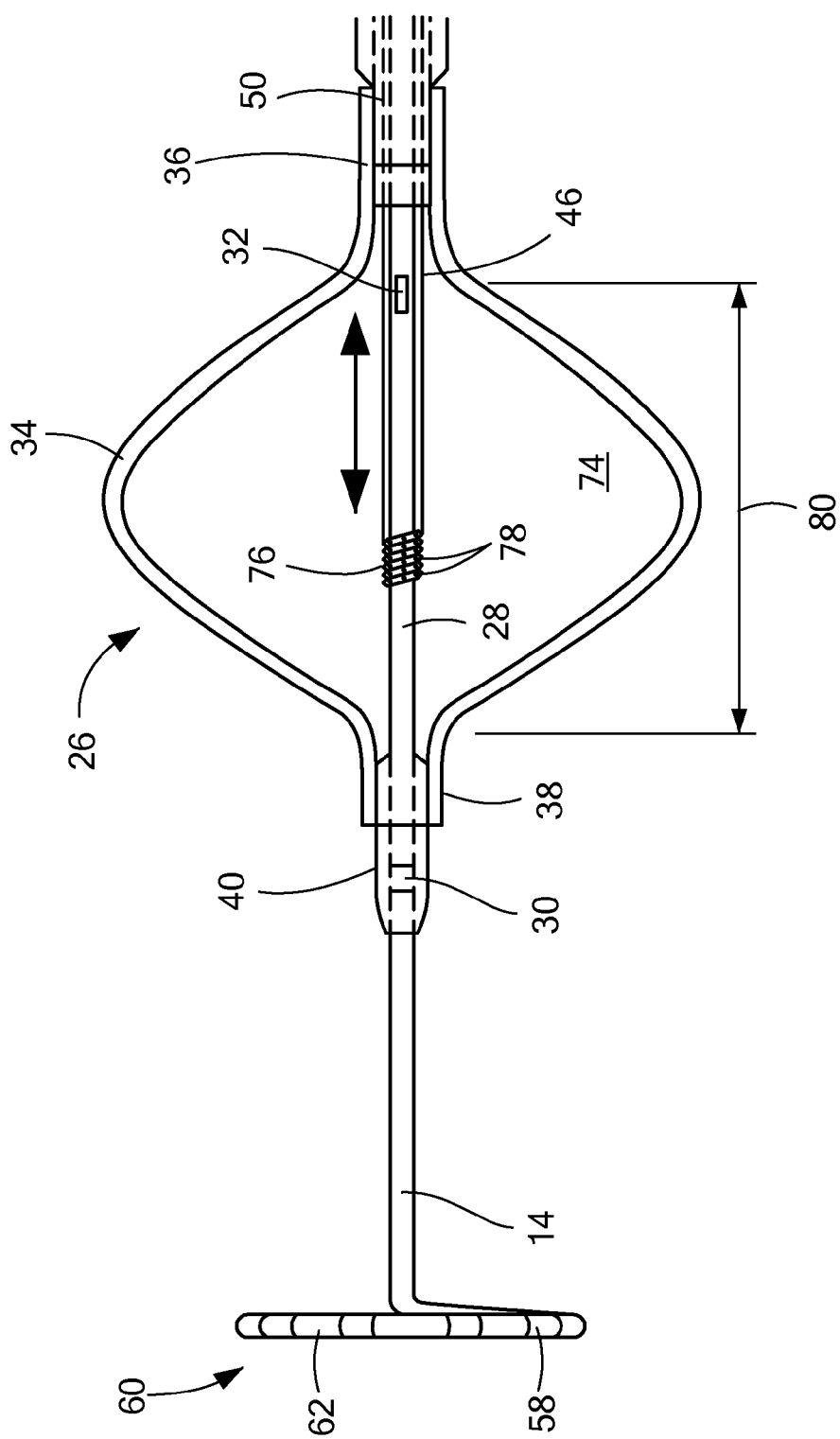
FIG. 2 shows a distal portion of an exemplary cryotreatment catheter.

The cryotreatment catheter 12 may generally include a handle 18, an elongate body 20 having a distal portion 22 and a proximal portion 24, one or more treatment elements 26, a guide wire lumen 28, a distal temperature sensor 30, a proximal temperature sensor 31, and a temperature sensor 32 within the treatment element. Further, the cryotreatment catheter 12 may have a longitudinal axis 33. The treatment element 26 may be a cryoballoon 34, as shown in FIGS. 1-3. The cryoballoon 34 may be coupled to the distal portion 22 of the elongate body 20 of the cryotreatment catheter 12. For example, the cryoballoon 34 may define a proximal portion or neck 36 that is affixed to or coupled to the distal portion 22 of the elongate body 20, and may further define a distal portion or neck 38 that is affixed to or coupled to the guide wire lumen 28 (such as the distal portion 40 of the guide wire lumen 28). However, it will be understood that the cryoballoon 34 may be coupled, affixed, disposed on, integrated with, or otherwise attached to the elongate body 20 and/or the guide wire lumen 28. Additionally, multiple cryoballoons may be used, such as when the cryoballoon 34 is disposed within or without a second cryoballoon (not shown). The guide wire lumen 28 may lie along the longitudinal axis 33 and be longitudinally movable within the elongate body 20. In this manner, longitudinal movement of the guide wire lumen 28 will affect the shape of the cryoballoon 34. The proximal portion of the guide wire lumen 28 may be in mechanical communication with one or more steering mechanisms 44 in the handle 18 of the cryotreatment catheter 12, such that the guide wire lumen 28 may be longitudinally extended or retracted using one or more steering mechanisms 44, such as knobs, levers, wheels, pull cords, and the like.

In addition to the guide wire lumen 28, the cryotreatment catheter 12 may include one or more lumens. As shown in FIG. 2, the cryotreatment catheter 12 may include a fluid injection lumen 46 in fluid communication with a coolant supply reservoir 48, and a coolant recovery lumen 50 in fluid communication with a coolant recovery reservoir 52. Further, the coolant recovery lumen 50 may be in communication with a vacuum 54 to facilitate removal of fluid from the cryoballoon 34 (for example, expanded coolant). If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator 56.

The mapping catheter 14 may be passable (longitudinally movable) through the guide wire lumen 28. The mapping catheter 14 may include one or more pairs of mapping elements 58, such as electrodes capable of sensing and recording electrograms from cardiac tissue. The one or more pairs of mapping elements 58 may be composed of metal or other electrically conductive material and may be affixed on an outer surface of the mapping catheter 14, integrated and flush with the body of the mapping catheter 14 (such that the mapping catheter has a smooth outer surface), may be areas of exposed electrically conductive material (for example, where an outer insulative layer has been removed), or may be otherwise affixed, coupled to, or integrated with the mapping catheter 14. The mapping catheter 14 may be in deformable and/or steerable using one or more steering mechanisms 44 into a variety of configurations. For example, the distal portion 60 of the mapping catheter 14 may be deformable into a lasso-type configuration, such that the loop portion 62 and mapping elements 58 may be in contact with at least a portion of an inner circumference of a PV.

The console 16 may be in electrical and fluid communication with the cryotreatment catheter 12 and the mapping catheter 14, and may include one or more fluid (for example, cryotreatment coolant) reservoirs 48, coolant recovery reservoirs 52, energy generators 56, and computers 66 with displays 68, and may further include various other displays, screens, user input controls, keyboards, buttons, valves, conduits, connectors, power sources, processors, and computers for adjusting and monitoring system 10 parameters. As used herein, the term "computer" may refer to any programmable data-processing unit, including a smart phone, dedicated internal circuitry, user control device, or the like. The computer 66 may include one or more processors 70 that are in electrical communication with the one or more pairs of mapping elements 58, the one or more sensors 30, the one or more treatment elements 26, and one or more valves 72 and programmable to execute an algorithm for locating one or more optimal treatment areas, for controlling the temperature of the one or more treatment elements 26, for generating one or more displays or alerts to notify the user of various system criteria or determinations, and/or for predicting temperature within target tissue based at least in part on signals from one or more of the temperature sensors 30, 31, 32. As a non-limiting embodiment, the proximal portion of the mapping catheter 14 may include an electrical connection that is matable to at least a portion of the console (for example, with the electrophysiology recording equipment) and in electrical communication with the one or more processors 70.

The console 16 may also include one or more valves 72 that are in electrical and/or mechanical communication with, and controllable by, the console 16. For example, the computer 66 and/or one or more processors 70 may be programmable to control various system components, such as the one or more valves 72, to operate according to a duty cycle that includes opening and closing the one or more valves 72 to regulate the flow of coolant through the system 10 and the catheter 12, and to thereby regulate the temperature of the treatment element 26 (for example, the cryoballoon 34). The duty cycle may be programmable by the user and/or may be automatically set by the console 16 according to a predicted tissue temperature based at least in part on signals from one or more of the temperature sensors 30, 31, 32. Although the valves 72 are shown as being located in the console 16 in FIG. 1, it will be understood that one or more valves may be located in other parts of the system, including within the catheter 12 itself.

Referring now to FIG. 2, a distal portion of an exemplary cryotreatment catheter is shown. As shown and described in FIG. 1, the catheter 12 may include a cryoballoon 34 having a proximal neck 36 coupled to the distal portion 22 of the elongate body 20 and a distal neck 38 coupled to the distal portion 40 of the guide wire lumen 28. However, it will be understood that the cryoballoon 34 may be coupled to the elongate body 20 and/or guide wire lumen 28 in other suitable configurations. Further, the treatment element 26 may include more than one cryoballoon 34, such as when a first cryoballoon is disposed within a second cryoballoon (not shown). Such a configuration may enhance patient safety, as the outer balloon may prevent coolant from entering the patient's bloodstream if the inner balloon developed a leak. The cryoballoon 34 may also include an inner chamber 74 in which coolant is expelled from the fluid injection lumen 46 through one or more fluid injection elements 76. For example, the coolant injection element 76 may include a conduit that is wrapped around the guide wire lumen 28 in one or more coils, and may have a plurality of injection apertures 78 (as shown in FIGS. 1 and 2). Coolant expelled into the inner chamber 74 may be drawn from the chamber 74 and into the fluid recovery lumen 50 by the negative pressure environment generated by the vacuum 54, with which the fluid recovery lumen 50 may be in fluid communication. Recovered coolant may be vented to the atmosphere or collected in the coolant recovery reservoir 52. Although the treatment element 26 is shown and described herein as being a cryoballoon 34, it will be understood that the treatment element 26 may be any structure capable of ablating tissue and completely occluding a pulmonary vein.

The catheter 12 may further include a distal temperature sensor 30, a proximal temperature sensor 31, and a temperature sensor 32 disposed within the cryoballoon 34. As a non-limiting example, the temperature sensors may be thermocouples, thermistors, or resistance thermometer (RTD).

The distal portion 40 of the guide wire lumen 28 may extend beyond the inner chamber portion 80 of the cryoballoon 34, giving the distal portion of the catheter 12 a "nose" 82. That is, the distal portion 40 of the guide wire lumen 28 defines a nose 82 that extends beyond the inner chamber portion 80 of the cryoballoon 34. The distal temperature sensor 30 may be located on the nose 82, at distance $d_1$ from the inner chamber portion 80 of the cryoballoon 34. As a non-limiting example, $d_1$ may be between approximately 1 mm and approximately 3 mm. Likewise, the distance $d_2$ between the proximal sensor 31 and the inner chamber portion 80 of the cryoballoon 34 may be between approximately 1 mm and approximately 3 mm. Such distances may enable each temperature sensor 30, 31 to measure an accurate environmental temperature that is not unduly influenced by either the temperature of the cryoballoon (for example, if the sensors 30, 31 are too close to the cryoballoon 34) or the surrounding flow of warm blood (for example, if the sensors 30, 31 are too far from the cryoballoon 34). Although the distal neck 38 may extend beyond the inner chamber portion 80 of the cryoballoon 34 to enhance attachment of the balloon 34 to the distal portion 40 of the guide wire lumen 28, the distal neck 38 may terminate proximal of the distal temperature sensor 30 to prevent the distal neck 38 from interfering with the functionality of the temperature sensor 30. Likewise, the proximal temperature sensor 31 may be located on the distal portion 22 of the elongate body 20, at distance $d_2$ from the inner chamber portion 80 of the cryoballoon 34. The sensor 31 may be located proximal to the proximal neck 36 of the cryoballoon 34 to prevent the proximal neck 36 from interfering with the functionality of the temperature sensor 31.

The temperature sensor 32 may be disposed within the inner chamber 74 of the cryoballoon 34. This interior sensor 32 may be used to monitor the temperature of coolant within the cryoballoon 34, and may be located at any suitable position within the balloon 34. For example, the sensor 32 may be affixed to an inner surface of the cryoballoon 34 (as shown in FIG. 2) or to the guide wire lumen 28 (as shown in FIG. 1), such as with an adhesive or bonding agent.

The mapping catheter 14 may be longitudinally movable within the guide wire lumen 28, so that the mapping catheter 14 may be extended and retracted relative to the cryotreatment catheter 12. Before cryotreatment is initiated, the mapping catheter 14 may be positioned within the PV proximate the PV ostium where electrical signals may be present, such that at least one pair of mapping elements 58 may detect and record pulmonary vein potentials (PVPs). The mapping catheter 14 may also be used to detect and record PVPs during and/or after the procedure. The presence of PVPs may indicate that the treatment has not destroyed or interrupted the aberrant electrical conduction pathways and that additional treatment may be required.

Figure 3A:
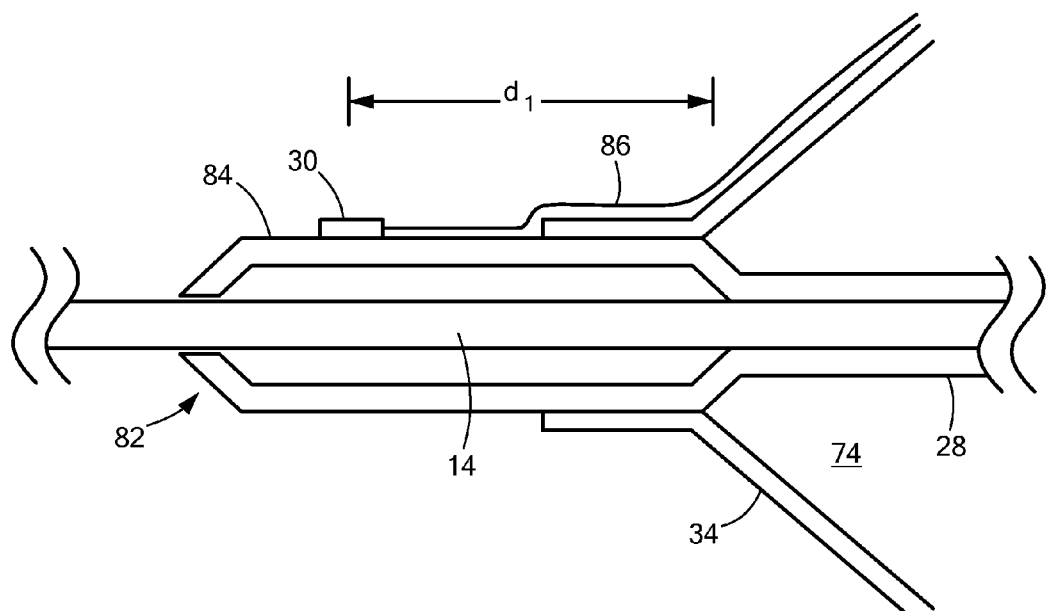
FIG. 3A shows a first embodiment of a way in which a temperature sensor may be coupled to a cryotreatment catheter.

Referring now to FIGS. 3A-3E, different embodiments of ways in which a temperature sensor may be coupled to a cryotreatment catheter. In the first embodiment shown in FIG. 3A, the distal temperature sensor 30 may be coupled to an outer surface of the nose 82. Although FIG. 3A shows the distal temperature sensor 30 protruding from the outer surface 84 of the nose 82, the figures may not be drawn to scale and the temperature sensor 30 may be thin enough that the sensor 30 lies flush or substantially flush with the outer surface 84 of the nose 82. Alternatively, the sensor 30 may be placed within a recessed area of the nose 82, thereby causing the sensor 30 to lie flush or substantially flush with the outer surface 84 of the nose 82. The sensor 30 may be a discrete sensor (that is, not be configured as a band or array of sensors) and may include one or more wires 86 that transmit signals (for example, temperature measurements by the sensor 30) to the console, and the wires 86 may be disposed along the outer surface of the catheter 12, over the cryoballoon 34 and elongate body 20, but may be disposed within the handle 18. Although the wires 86 are shown a small distance from the outer surface of the device for clarity, it will be understood that the wires 86 may be in contact with the device, and may be affixed (for example, adhered, bonded, or coupled) to one or more outer surfaces of the device so that the wires 86 do not become snagged or pulled during a procedure. The handle 18 may be in electrical communication with the console 16, thereby establishing an electrical communication between the wires 86 and the console 16.

Figure 3B:
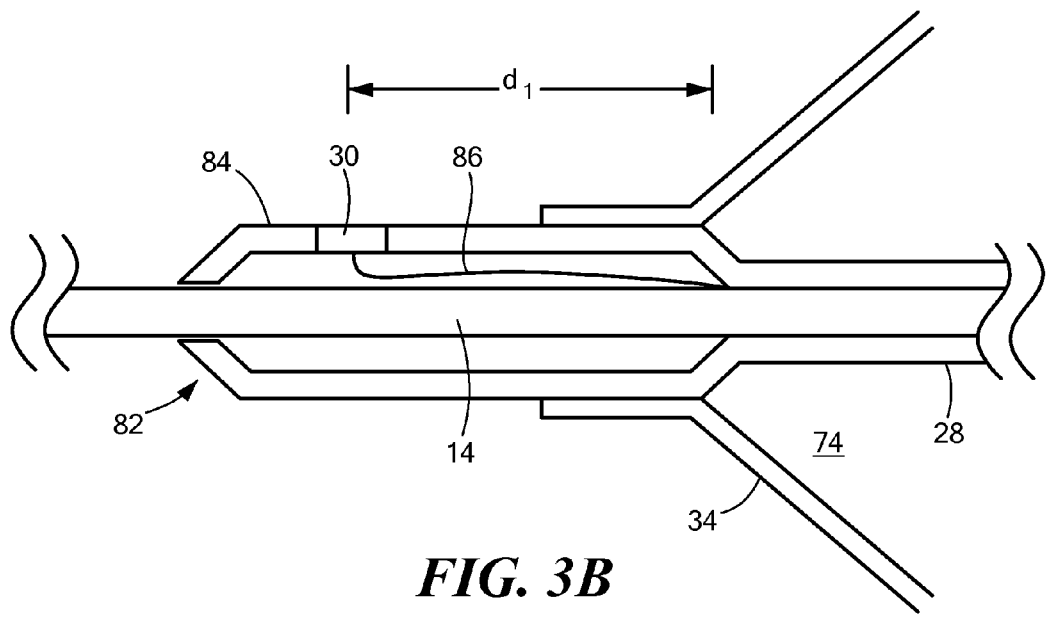
FIG. 3B shows a second embodiment of a way in which a temperature sensor may be coupled to a cryotreatment catheter.

In the second embodiment shown in FIG. 3B, the distal sensor 30 may be a discrete sensor and may be disposed within the guide wire lumen 28, but may protrude from the outer surface 84 of the nose 82. Alternatively, the temperature sensor 30 may be thin enough that the sensor 30 lies flush or substantially flush with the outer surface 84 of the nose 82 (as shown in FIG. 3B). The one or more wires 86 may be disposed within the guide wire lumen 28, and may travel the length of the device within the guide wire lumen 28 to the handle 18, and may also be disposed within the handle 18 and in electrical communication with the console as described in FIG. 3A.

Figure 3C:
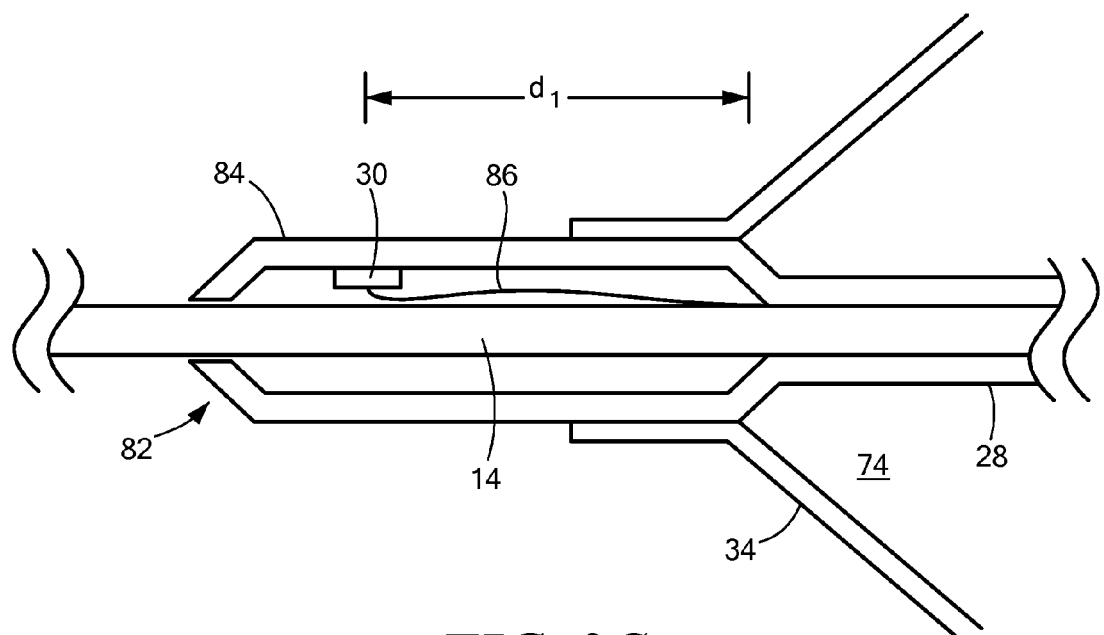
FIG. 3C shows a third embodiment of a way in which a temperature sensor may be coupled to a cryotreatment catheter.

In the third embodiment shown in FIG. 3C, the distal sensor 30 may be entirely disposed within the guide wire lumen 28, such that temperature measurements may be taken through the material of the guide wire lumen. In such an embodiment, the thickness of the wall of the guide wire lumen 28 may be thinnest proximate the distal sensor 30 to facilitate temperature measurement of the outside environment. The sensor's electrical wires 86 may be disposed within the guide wire lumen 28, and may travel the length of the device within the guide wire lumen 28 to the handle 18, and may also be disposed within the handle 18 and in electrical communication with the console as described in FIG. 3A.

Figure 3D:
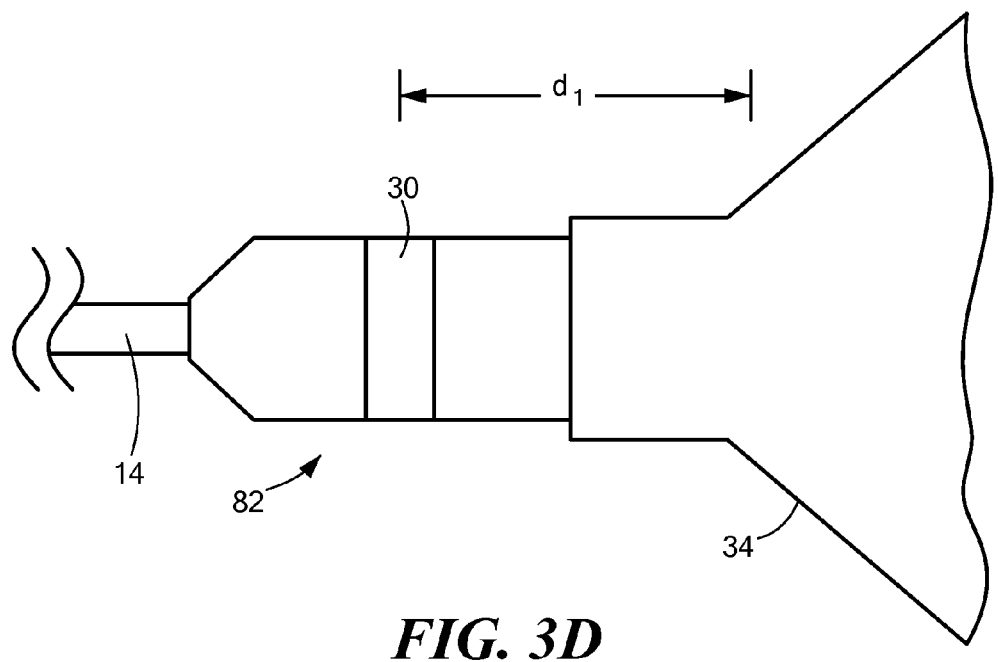
FIG. 3D shows a fourth embodiment of a way in which a temperature sensor may be coupled to a cryotreatment catheter.

In the fourth embodiment shown in FIG. 3D, the distal sensor 30 may be a band-shaped sensor that entirely or partially encircles the outer diameter of the nose 82. As in the embodiments of FIGS. 3A and 3B, the band-shaped temperature sensor 30 may protrude from the outer surface 84 of the nose 82 or may lie flush or substantially flush with the outer surface 84 of the nose 82. Additionally, the sensor's electrical wires 86 may be located either on the outside of the catheter 12 (as shown and described in FIG. 3A) or within the catheter 12 (as shown and described in FIGS. 3B and 3C).

Figure 3E:
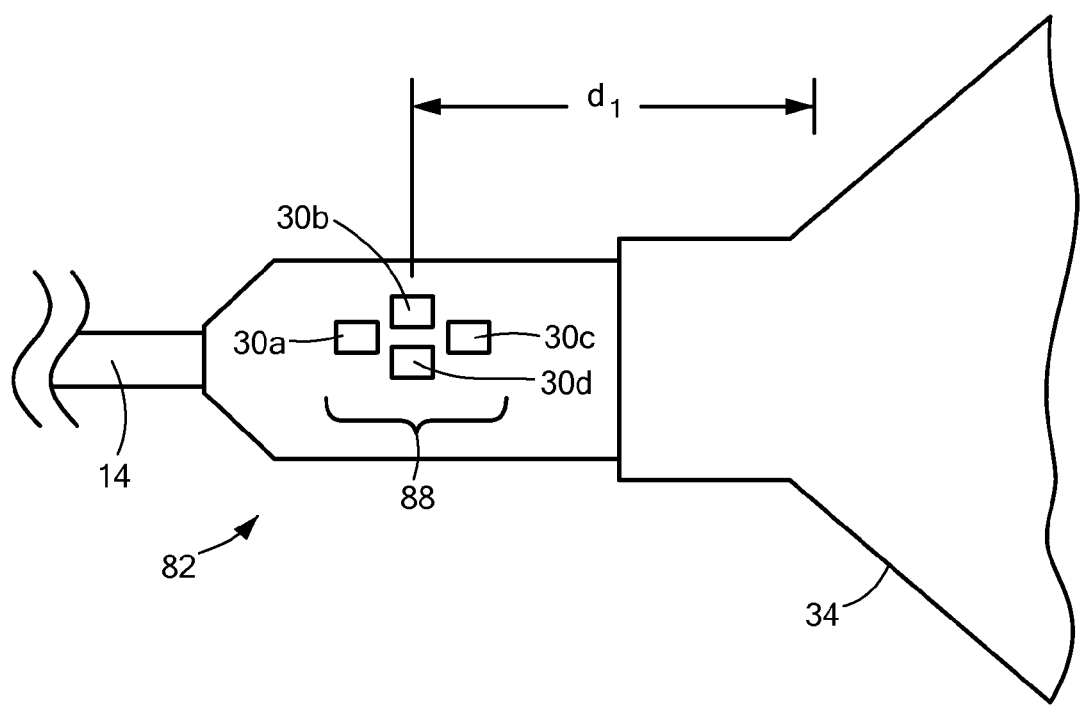
FIG. 3E shows a fifth embodiment of a way in which a temperature sensor may be coupled to a cryotreatment catheter.

In the fifth embodiment shown in FIG. 3E, the distal temperature sensor 30 may be an array 88 of sensors (30a, 30b, 30c, 30d . . . ). The array 88 and the one or more electrical wires 86 may be disposed on an outer surface 84 of the nose 82 or within the guide wire lumen 28, as shown and described in FIGS. 3A-3D. Further, the array 88 may include one or more discrete sensors, band-shaped sensors, or combination thereof. For all embodiments in FIGS. 3A-3E, the sensors 30 may be affixed or coupled to one or more components of the catheter 12 by means such as biocompatible adhesives and/or bonding agents. Additionally, the discrete sensors may have any shape, such as elongate, round, square, rectangular, polygonal, dome shaped, faceted, or the like. Likewise, the outer surface of the band-shaped sensors may be flat, rounded, faceted, or the like. Further, the sensor 30, 31, 32 and its one or more wires 86 may be manufactured from the same piece of material, such that the sensor 30, 31, 32 has an elongate wire-like shape.

The proximal temperature sensor 31 may be configured as shown and described in any of FIGS. 3A-3E, except that the proximal sensor 31 may be located on or within the elongate body 20 rather than the guide wire lumen 28.

Figure 4:
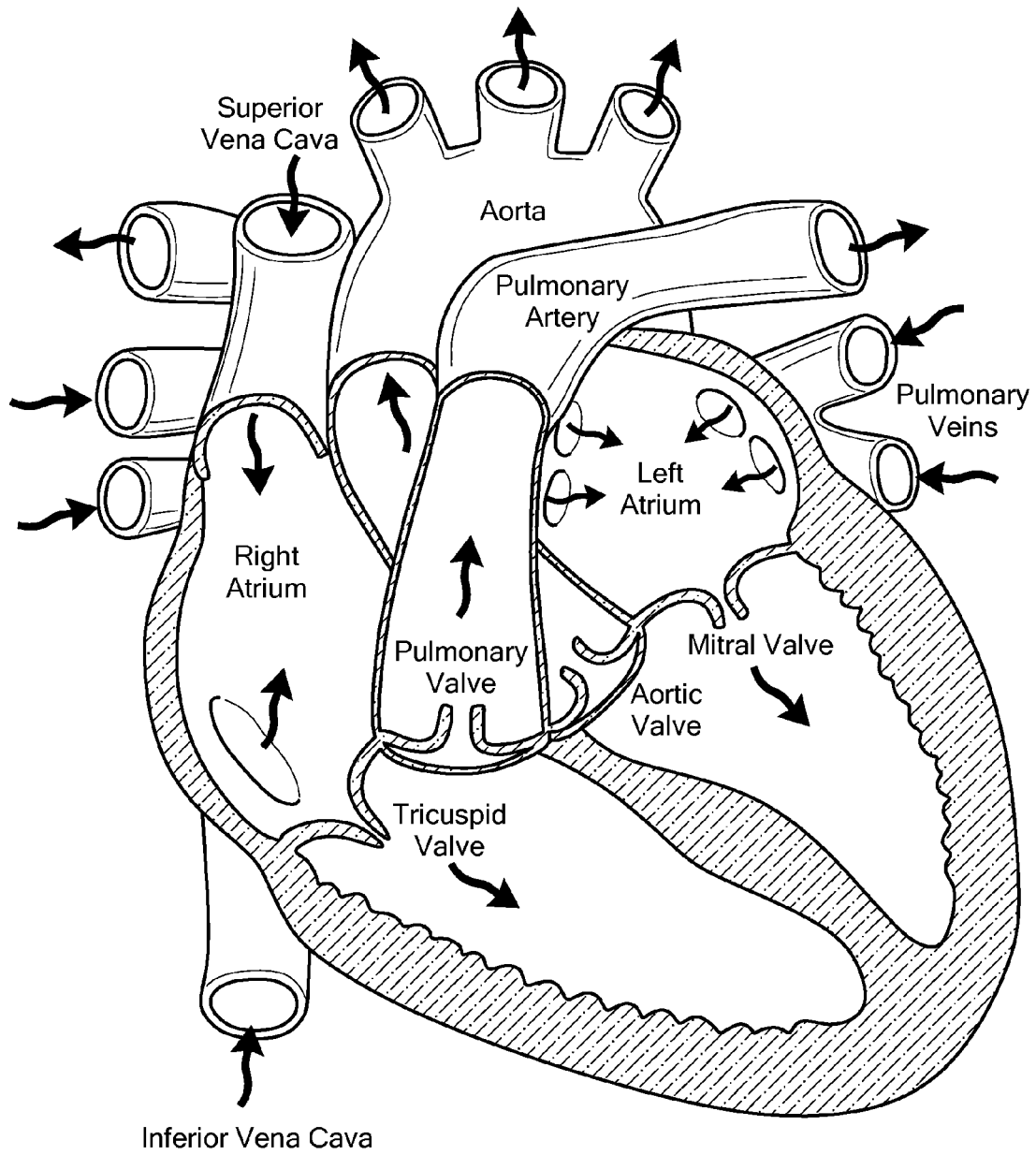
FIG. 4 shows a stylized representation of the heart, including pulmonary vein ostia.

Referring now to FIG. 4, a stylized representation of a heart is shown. The heart may generally include a right atrium (RA), left atrium (LA), right ventricle (RV), and left ventricle (LV). On the left side of the heart, the superior vena cava and inferior vena cava introduce deoxygenated blood from the body into the RA, from where the blood flows through the tricuspid valve, into the LV, and exits the heart through the pulmonary valve into the pulmonary artery. The pulmonary artery carries deoxygenated blood from the heart to the lungs. On the right side of the heart, the pulmonary veins (PVs) introduce oxygenated blood from the lungs into the LA, from where the blood flows through the mitral valve, into the RV, and exits the heart through the aortic valve into the aorta. The aorta distributes oxygenated blood to all parts of the body.

Figure 5:
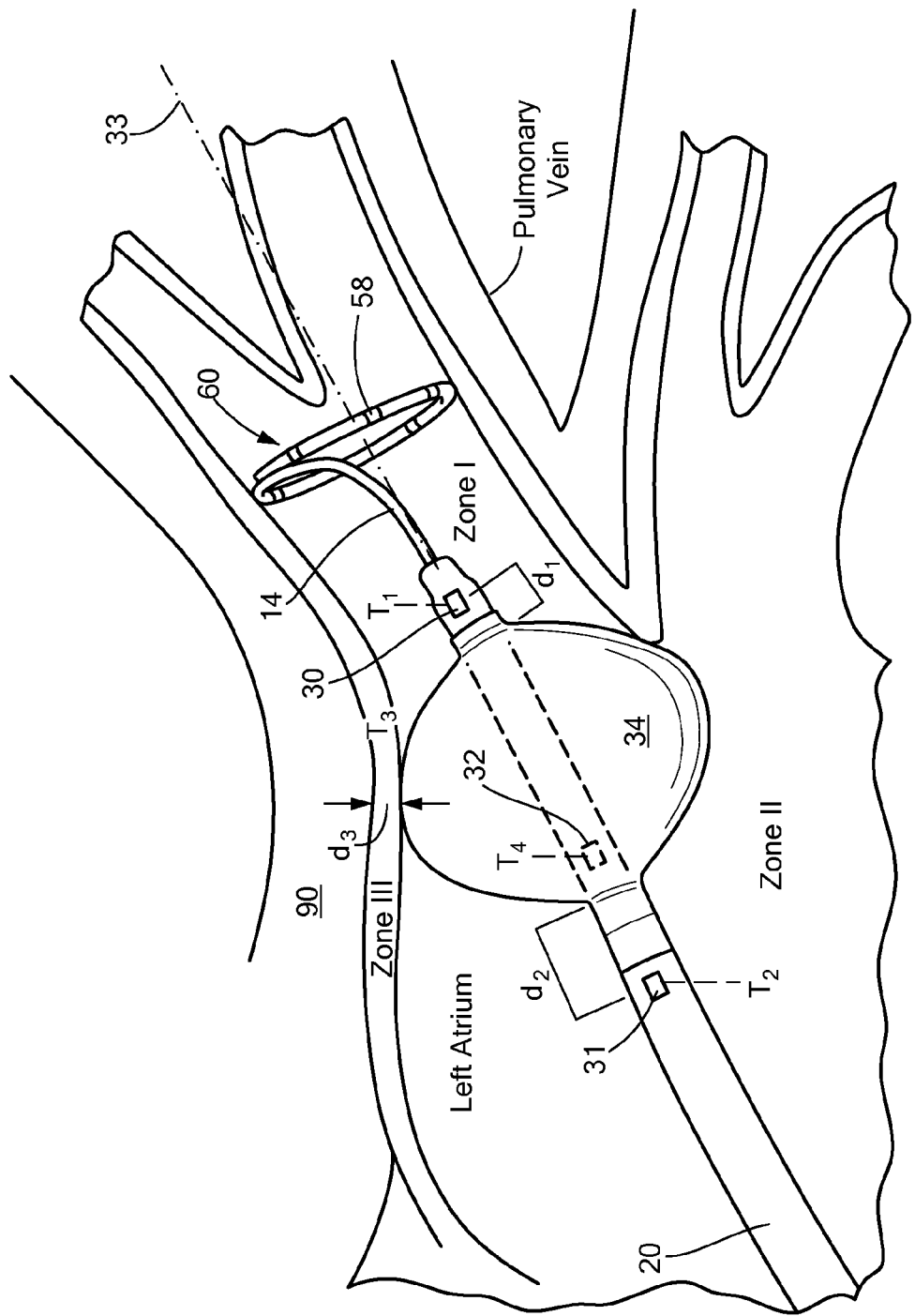
FIG. 5 shows occlusion of a pulmonary vein by a cryotreatment catheter.

Referring now to FIG. 5, a cryotreatment catheter is shown occluding a pulmonary vein for a pulmonary vein isolation (PVI) procedure is shown. The method may not include a step of confirming that a conduction block has been achieved, in which case the method may be termed a pulmonary vein ablation procedure. As used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. The inflated cryoballoon 34 may be positioned at the pulmonary vein (PV) ostium to occlude the PV, or block the flow of blood from the PV into the left atrium (LA) of the heart. Occlusion of the PV not only serves to position the cryoballoon 34 to create a circumferential lesion around the PV ostium and/or on the PV antrum, but also prevents warm blood from flowing over the portions of the cryoballoon 34 that are in contact with the target tissue, thereby enhancing the ability of the cryoballoon 34 to reach sufficiently cold temperatures for creating permanent cryoablation lesions on or in the target tissue. If the PV is not completely occluded, blood flow past the cryoballoon 34 may have the effect of raising the temperature of the cryoballoon 34, possibly resulting in the formation of reversible lesions on or in the target tissue. The blocked blood within the PV may be referred to as "stagnant" blood, whereas the blood within the LA may be referred to as "flowing" blood, as blood may still enter the LA from the other three PVs that are not being occluded by the catheter 12.

As shown in FIG. 4, the cryoballoon 34 may be positioned at the PV ostium such that the nose 82 of the catheter 12 is disposed within the PV, within the stagnant blood (Zone I). Therefore, the distal temperature sensor 30 may continuously measure the temperature $T_1$ of the stagnant blood in Zone I. In contrast, at least part of the distal portion 22 of the elongate body 20 may be disposed within the LA, within the flowing blood (Zone II). Therefore, the proximal temperature sensor 31 may continuously measure the temperature $T_2$ of the flowing blood in Zone II. The temperature sensor 32 may continuously measure the temperature $T_4$ within the inner chamber 74 of the cryoballoon 34. The target tissue (for example, within the PV ostium) may have a thickness, $d_3$, within which tissue ablation is desired. Tissue within the thickness $d_3$ is referred to as being within Zone III. Tissue located deeper below the surface than $d_3$ (that is, outside of Zone III) may be referred to as "collateral structures" 90. Ablation of or damage to the collateral structures 90 may not be desired. For example, thickness $d_3$ may be the thickness of the muscular sleeve of the PV ostium comprising myocardial tissue, within which ablation is desired, and the collateral structures 90 may generally include non-myocardial tissue and may specifically include the lungs, nerves, and the esophagus. Ablation and/or thermal effects beyond the myocardial tissue may not be desired, and may have damaging effects on surrounding structures. Although the collateral structures 90 are shown as generally following the shape of a pulmonary vein, the drawings are not necessarily drawn to scale and it will be understood that the collateral structures 90 may include non-cardiac structures. Thickness $d_3$ may be determined for each patient before a PVI or PVAI procedure, such as by using methods such as computed tomography (CT). Additionally or alternatively, thickness $d_3$ may be determined from literature concerned with PV ablation procedures. Although $d_3$ may vary from patient to patient, $d_3$ may generally be approximately 2.2 mm±0.8 mm. Likewise the temperature at which a permanent lesion will form in the target tissue, $T_3$, may be determined for a particular target tissue experimentally or from literature concerned with cryoablation procedures. Although this temperature may vary from patient to patient and between the cellular, tissue, and organ levels, generally, permanent lesions may be formed in myocardial tissue at temperatures of approximately −20° C. and below.

Figure 6:
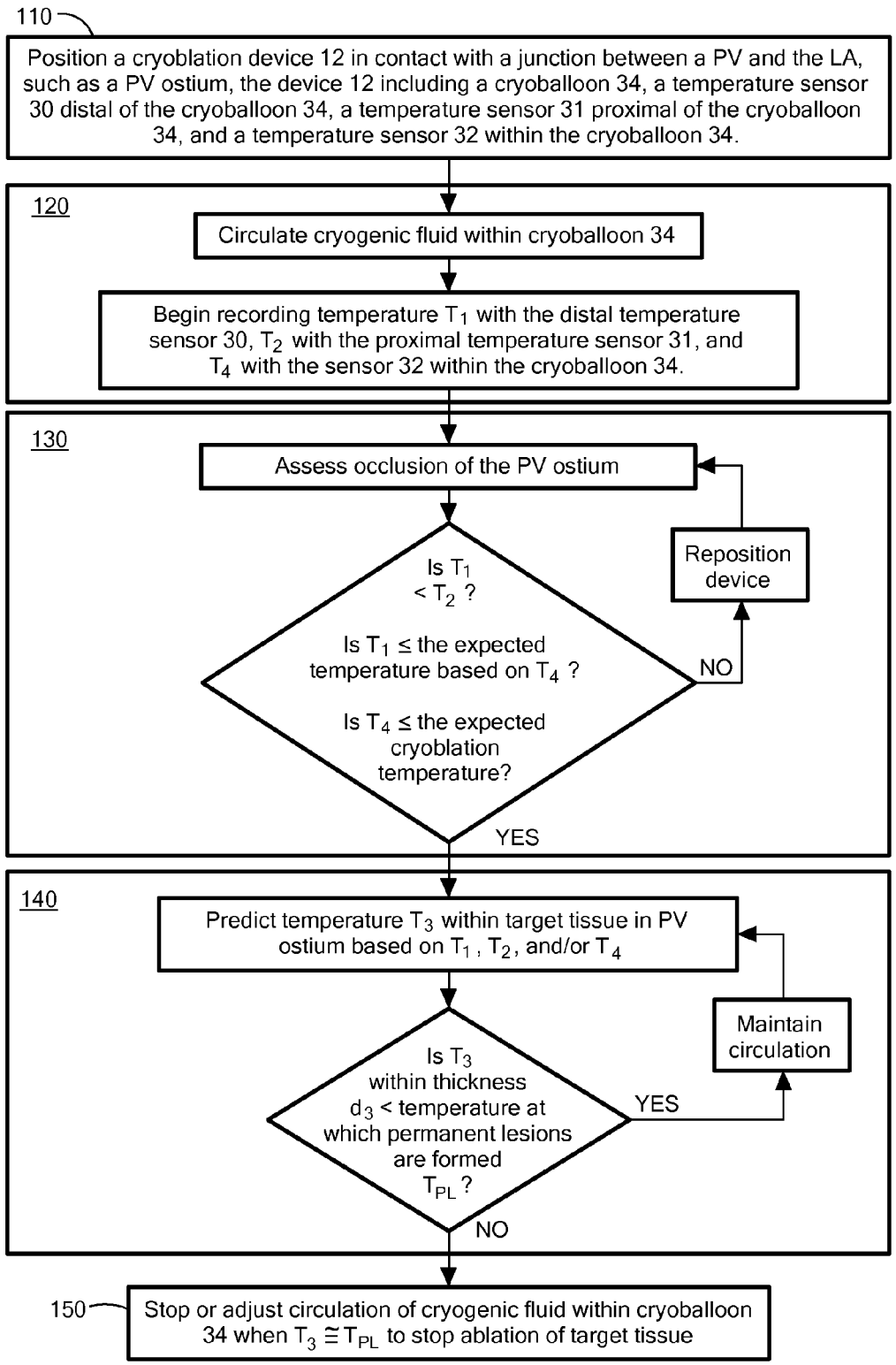
FIG. 6 shows a flowchart for a method of real-time lesion assessment during a cryoablation procedure.

Referring now to FIG. 6, a flowchart for a method of real-time lesion assessment during a cryoablation procedure is shown. The method of the present invention may be used to predict a temperature $T_3$ within a target tissue having a depth $d_3$, based at least in part on temperature measurements recorded and transmitted to the console 16 by a distal temperature sensor 30 located a known distance from the cryoballoon 34, a proximal temperature sensor 31 located a known distance from the cryoballoon 34, and/or a temperature sensor 32 located within the cryoballoon 34. In vitro experimentation (such as that shown and described in FIG. 7) may be used to generate data from which a transfer function ($f_T$) may be extrapolated. For example, empirical data may be used to create a set of reference temperatures that may be used in, for example, chart, look-up table, or algorithm format to correlate a temperature sensed by the device 12 (for example, $T_1$, $T_2$, or $T_3$) with a real-time target tissue temperature, $T_3$. Alternatively, the empirical data may be generated using in vivo experimentation. The transfer function may be defined as the relationship between a sensed temperature or rate of change in a sensed temperature and the real-time temperature or rate of change of real-time temperature in target tissue (that is, tissue within thickness $d_3$, or Zone III). The transfer function $f_T$ may be a linear relationship or a complex functional relationship. Further, the one or more processors 70 of the computer 66 (or other console component in communication with the temperature sensors that is capable of executing an algorithm) may be programmable to execute an algorithm that uses a transfer function to adjust one or more sensed temperature or changes in temperature and communicate the real-time tissue temperature and/or lesion formation status to the user (for example, using one or more displays 68). Thus, a user does not need to directly measure or monitor the temperature of the target tissue during a cryoablation procedure. Rather, the real-time temperature of the target tissue, and therefore the status of lesion formation therein or thereon, may be determined using by adjusting one or more sensed temperatures at a known distance from the cryoballoon (and/or within the cryoballoon) with the transfer function $f_T$. For example, if experimental data determined that the temperature within thickness $d_3$ is 2.5 times the temperature sensed by the distal temperature sensor 30 ($T_1$):

$$T_3 = T_1 \times F_T$$

$$T_3 = -10° \text{ C.} \times 2.5$$

$$T_3 = -25° \text{ C.}$$

It will be understood that the above example is illustrative only, and may not be the actual relationship between $T_3$ and $T_1$. Additionally, the calculation of $T_3$ may also take into account the temperature within the cryoballoon, $T_4$.

The method of the present invention may also be used to assess whether a pulmonary vein (PV) is completely occluded by the cryoballoon 34 based at least in part on temperature measurements recorded and transmitted to the console 16 by a distal temperature sensor 30 located a known distance from the cryoballoon 34, a proximal temperature sensor 31 located a known distance from the cryoballoon 34, and/or a temperature sensor 32 located within the cryoballoon 34. In one method, the one or more processors 70 of the computer 66 (or other console component in communication with the temperature sensors that is capable of executing an algorithm) may be programmable to execute an algorithm that compares a sensed temperature or rate of change in temperature by the distal sensor 30 with a sensed temperature or rate of change in temperature by the proximal sensor 31 to determine whether the PV is completely occluded. When the device 12 is positioned in contact with a PV ostium, the distal temperature sensor 30 may be disposed within the PV (Zone I). Conversely, the proximal temperature sensor 31 may be disposed within the left atrium (LA) (Zone II). When the PV is completely occluded, blood does not flow past the cryoballoon and into the LA and, as a result, the PV near the cryoballoon becomes filed with stagnant (i.e. non-flowing) blood. The supply of stagnant blood is not continuously refreshed by warm, flowing blood, and the temperature ($T_1$) of the stagnant blood may be reduced when the cryoballoon is activated for treatment. That is, the cold cryoballoon will cool the stagnant blood. In contrast, the flowing blood within the LA remains a constant temperature of approximately 37° C. ($T_2$). If complete occlusion is not achieved, the temperature of blood within the PV may be the same or approximately the same as the temperature of blood within the LA: $T_1 = T_2$ or $T_1 \approx T_2$. The one or more processors 70 may be programmable to execute an algorithm that compares $T_1$ to $T_2$ and correlates the difference to either a binary "yes-or-no" occlusion determination or to a degree of occlusion.

Additionally or alternatively, $T_1$ may be compared to the expected temperature at $d_1$ based on the temperature, $T_4$, measured by sensor 32 within the cryoballoon 34. As a non-limiting example, if $T_4$ is $-50°$ C. whereas $T_1$ is only $-10°$ C., the PV may not be completely occluded and warm blood may be flowing past the sensor 30 and the cryoballoon 34. Still further, $T_4$ may be compared with the expected temperature within the cryoballoon 34 based on experimental data or from the literature or product specifications. If $T_4$ is less than the expected temperature, the PV may not be completely occluded and warm blood may be flowing past and warming the cryoballoon 34. These methods of occlusion assessment may eliminate the need to eject contrast medium from the device 12 into the PV to confirm occlusion, thereby reducing or eliminating the patient's exposure to the medium itself and the x-ray radiation used to visualize the medium.

Referring now to FIG. 6 in detail, the first step 110 of the method may include positioning the cryoablation device 12 in contact with a junction between as PV and the LA, such as a PV ostium. As shown and described in FIGS. 1-3E and 5, the device 12 may include a treatment element 26, such as a cryoballoon 34. The device 12 may also include a temperature sensor 30 distal of the cryoballoon 34, a temperature sensor 31 proximal of the cryoballoon 34, and a temperature sensor 32 located within the cryoballoon 34. Once the device 12 is positioned in contact with the target tissue, for example, the PV ostium, the circulation of a coolant within the cryoballoon 34 may be initiated. After (and, optionally, before) the coolant has begun to circulate within the cryoballoon 34, the temperature sensors 30, 31, 32 may continuously measure the temperature of the environment proximate the sensor (second step 120). For example, the distal sensor 30 may measure the temperature and/or change in temperature of the blood within the PV in Zone I ($T_1$), the proximal sensor 31 may measure the temperature and/or change in temperature of the blood within the LA in Zone II ($T_2$), and the sensor 32 within the inner chamber 74 of the cryoballoon 34 may measure the temperature and/or change in temperature within the cryoballoon 34.

Complete occlusion of the PV by the cryoballoon 34 is desired before beginning the cryoablation procedure, because forming permanent lesions in or on the target tissue may be difficult or impossible if warm blood is allowed to flow over the cryoballoon 34 from the PV into the LA. Therefore, occlusion is assessed in the third step 130 of the method. There may be several ways in which occlusion may be assessed, all of which being based at least in part on one or more temperature measurements from sensors 30, 31, and/or 32. Further, any of the methods may be used alone or together, and one or more assessment algorithms may be executed by the one or more processors 70 and/or the measurement values may be displayed for a user on a display 68. First, a temperature measured within the PV, $T_1$, may be compared to a temperature measured in the LA, $T_2$. For example, if $T_1$ is greater than or equal to $T_2$, incomplete occlusion may be indicated. Conversely, if $T_1$ is less than $T_2$, complete occlusion may be indicated. Although not shown in FIG. 6, the rate of change in $T_1$, or $\Delta T_1$, may also be compared to a rate of change in $T_2$, or $\Delta T_2$. If $T_1$ (or $\Delta T_1$) is the same or substantially the same as $T_2$ (or $\Delta T_2$), then incomplete occlusion may be indicated. Second, $T_1$ may be compared to an expected temperature at a known distance from the cryoballoon 34 based on $T_4$ within the cryoballoon 34. If $T_1$ is greater than the expected temperature, incomplete occlusion may be indicated. Conversely, if $T_1$ is less than or equal to the expected temperature, complete occlusion may be indicated. Third, $T_4$ may be compared with an expected temperature within the cryoballoon 34 based at least in part on the lowest temperature that is possible for the device 12, system 10, and coolant, and/or the time over which the coolant has been circulating within the cryoballoon 34. If $T_4$ greater than the expected temperature, incomplete occlusion may be indicated. Conversely, if $T_4$ is less than or equal to the expected temperature, complete occlusion may be indicated. If one or more of these methods indicate that the PV is not completely occluded, the device 12 may be repositioned to reseat the cryoballoon 34 at the PV ostium. If the one or more processors 70 determine that complete occlusion has not been achieved, the one or more processors 70 may generate an alert, such as a visual or audio alert, to notify the use that the device 12 should be repositioned.

In the fourth step 140 of the method, the real-time temperature within thickness $d_3$ of the target tissue (Zone III) may be predicted and compared to the temperature, $T_{PL}$, at which a permanent lesion may be formed on or in target tissue. $T_{PL}$ may be determined based on the type of target tissue, thickness $d_3$ of the target tissue, from experimentation, from literature, and the like. The goal of cryoablation may be to thermally treat the target tissue at a temperature sufficient to create permanent lesions at a depth or thickness no greater than $d_3$. If ablation occurs at a depth greater than $d_3$ (outside of Zone III), unintended damage may occur to collateral structures 90. Therefore, a real-time tissue temperature $T_3$ or rate of change in temperature $\Delta T_3$ may be predicted by adjusting the measured temperature $T_1$ using a transfer function, as discussed herein with reference to FIG. 6. For example, the adjustment and comparison may be performed by the one or more processors 70 programmed to execute an appropriate algorithm. If the predicted real-time temperature within the target tissue is less than $P_{PL}$, the circulation of coolant through the cryoballoon 34 may be maintained, either automatically by the console or manually by the user. Once the predicted real-time temperature within the target tissue is equal or substantially equal (for example, within ±5° C.) to $T_{PL}$, the circulation of coolant may be stopped, adjusted, or minimized in order to increase the temperature of the cryoballoon 34 and to stop ablation of the target tissue (fifth step, 150). Optionally, the temperature of the cryoballoon 34 may be increased to a lesser degree (for example, the flow of coolant may be reduced by 10-30%, but not stopped altogether) if the predicted real-time temperature within the target tissue is within a pre-determined warning temperature range, or temperature that is getting close to but is not substantially equal to the $T_{PL}$. For example, the temperature of the cryoballoon 34 may be increased, such as by the adjustment of the flow of coolant, when the predicted real-time temperature is between approximately 5-10° C. less than $T_{PL}$. This may be done either automatically by the console 16 or manually by the user. Further, the console 16 may generate an alert, such as a visual alert or audio alert, that notifies the user that the target temperature has been reached within Zone III.

Figure 7A:
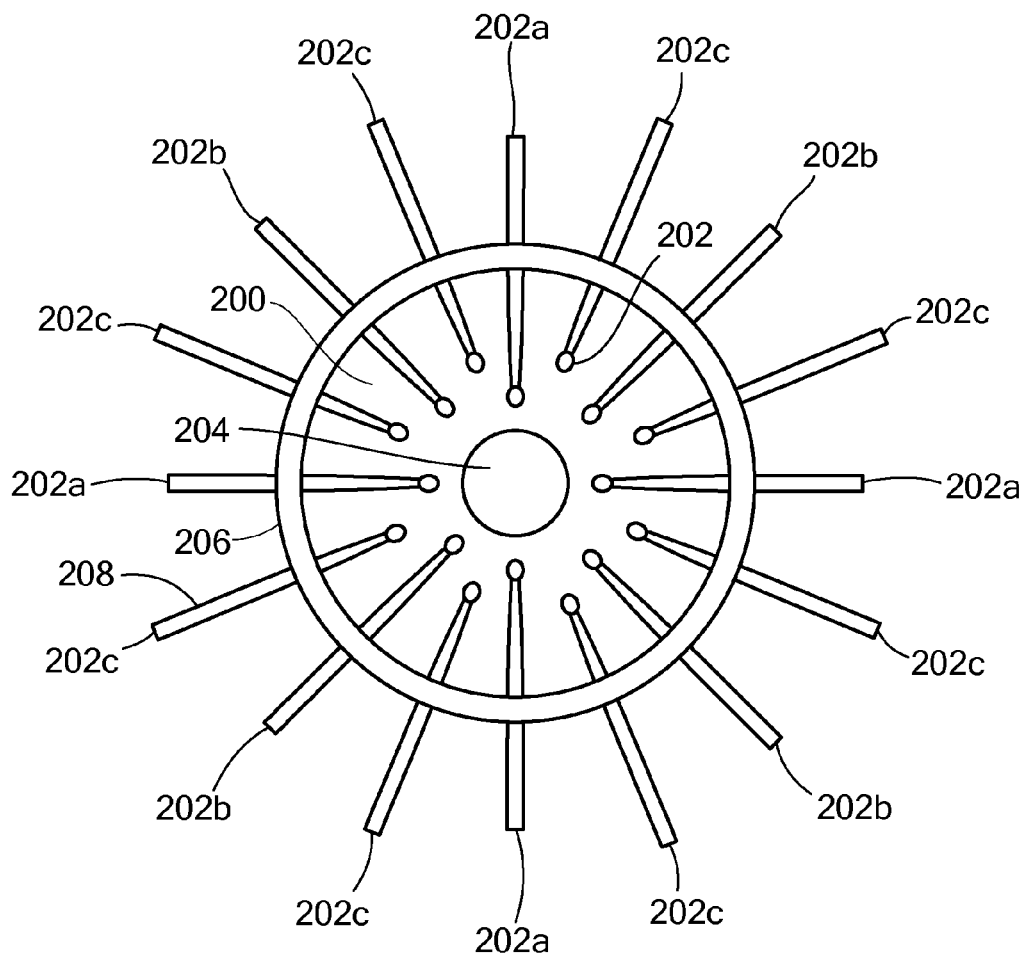
FIG. 7A shows an overhead view of an exemplary experimental setup for generating data from which to determine a transfer function.
Figure 7B:
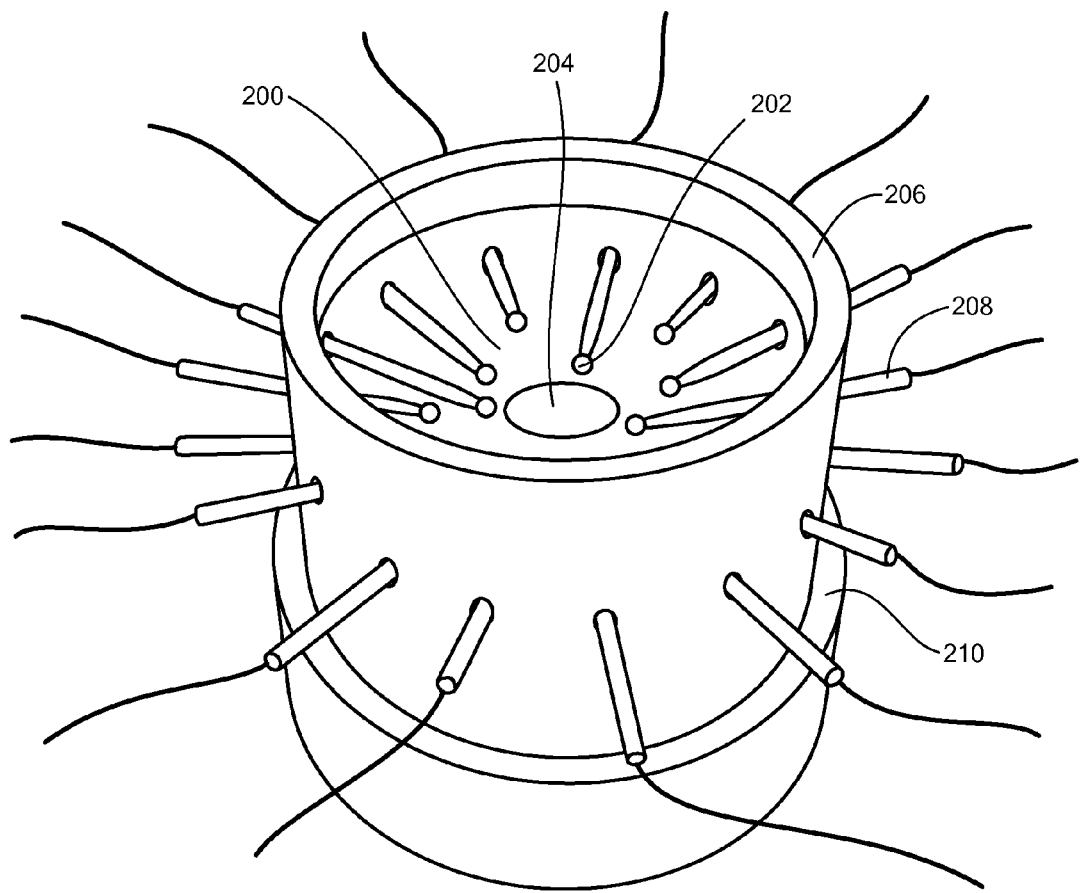
FIG. 7B shows a perspective view of the exemplary experimental setup of FIG. 7A.

Referring now to FIGS. 7A and 7B, an overhead view of an exemplary experimental setup that may be used to generate data from which to determine a transfer function is shown. In general, the experimental setup provides a means for measuring temperature within a tissue phantom 200 using a three-dimensional array of temperature sensors 202. Specifically, a plurality of temperature sensors 202 may be radially oriented within the tissue phantom 200 at various depths around a central lumen 204. Using this exemplary setup, temperature data at various depths within a target tissue may be compiled and used to generate a transfer function $f_T$, for example as discussed above regarding FIG. 6. This transfer function may then be used to correlate real-time target tissue temperatures at a variety of depths to temperatures measured by, for example, the distal temperature sensor 30. For example, when $T_1$ is a first value, the real-time temperature within the target tissue may be determined to be X° C. at a first depth within Zone III, Y ° C. within a second depth within Zone III, and Z ° C. at a tissue depth deeper than Zone III, within the collateral structure 90. The tissue phantom 200 may be composed of materials known in the art, and may be disposed within a frame 206 composed of, for example, plastic or metal. Each of the plurality of temperature sensors 202 may be disposed on an elongate metal or plastic tube 208 that is passed through the frame 206 and into the phantom tissue 200 at radial locations and at various depths within the phantom tissue 200 relative to the central lumen 204. The central lumen 204 may represent a hollow anatomical structure, such as a pulmonary vein. The frame 206 may be coupled to or integrated with a base 210, and a fluid having a temperature of approximately 37° C. (equal to or approximately equal to the temperature of human blood) may be circulated through the base 210 and/or the frame 206. Additionally or alternatively, a volume of fluid may be contained within the central lumen 204 of the tissue phantom 200, and may be in direct contact with the cryoballoon 34, sensor 30, and/or sensor 31 when the device is placed within the lumen 204. Thus, the fluid may simulate blood within a pulmonary vein during an in vivo procedure, enabling the distal sensor 30 to record a temperature data $T_1$ for correlation to $T_2$ and/or $T_3$ data.

As a non-limiting example, a first set of tubes 208 with sensors 202 (tube 208 and sensor 202 together referred to in FIG. 7A as 202a) may be located at approximately 1.0 mm, a second set of tubes 208 with sensors 202 (tube 208 and sensor 202 together referred to in FIG. 7A as 202b) may be located at approximately 2.5 mm, and a third set of tubes 208 with sensors 202 (tube 208 and sensor 202 together referred to in FIG. 7A as 202c) may be located at approximately 5.0 mm within the phantom tissue 200, measured from the surface of the phantom tissue 200 within the central lumen 204. The approximately 1.0 mm and 2.5 mm depths may be within Zone III, $d_3$, and the approximately 5.0 mm depth may be within the collateral structure 90. It will be understood that the sensors 202 and tubes 208 may have any configuration and/or orientation within the tissue phantom 200 and frame 206 suitable for gathering temperature data at any of a variety of depths within the tissue phantom 200, and are not limited to those shown in FIGS. 7A and 7B. Although not shown in the figures, data for generating a transfer function $f_T$ additionally or alternatively may be compiled from an experimental setup using living tissue, either within a body or explanted from the body.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for creating permanent lesions in target tissue proximate a junction between a pulmonary vein and a left atrium, the method comprising:

positioning a measuring device at least partially within the pulmonary vein;

obtaining a plurality of temperature measurements, with the measuring device, of blood at a location within the pulmonary vein; and comparing the plurality of temperature measurements to a set of reference temperatures that correlate temperature of the blood to tissue temperature to provide a real-time temperature within a target tissue.

2. The method of claim 1, wherein the measuring device comprises:
an occlusion element connectable to a source of coolant, circulation of coolant within the occlusion element causing the occlusion element to reach temperatures sufficient to ablate tissue;
a first temperature sensor located distal of the occlusion element; and
a second temperature sensor located within the occlusion element.

3. The method of claim 2, wherein the occlusion element is a cryoballoon.

4. The method of claim 2, wherein the target tissue has a thickness within which permanent cryoablation lesions may be created without damage to non-target tissue.

5. The method of claim 4, wherein the circulation of coolant within the occlusion element is adjusted when a determined temperature within the thickness is substantially the same as a temperature at which permanent lesions are formed within the target tissue.

6. The method of claim 5, wherein the circulation of coolant within the occlusion element is adjusted when the determined temperature is within ±5° C. of the temperature at which permanent lesions are formed within the target tissue.

7. The method of claim 5, wherein the circulation of coolant within the occlusion element is stopped when the determined temperature within the thickness is substantially the same as the temperature at which permanent lesions are formed within the target tissue.

8. The method of claim 5, wherein the circulation of coolant is reduced when a determined temperature within the thickness is substantially the same as the temperature at which permanent lesions are formed within the target tissue.

9. The method of claim 2, wherein the measured temperatures are correlated to the reference temperatures to determine a real-time temperature within the target tissue.

10. The method of claim 9, further comprising:
positioning the occlusion element at least partially within the pulmonary vein such that the first temperature sensor is disposed in the pulmonary vein and the second temperature sensor is disposed in a left atrium;
obtaining a first plurality of temperature measurements with the first temperature sensor and obtaining a second plurality of temperature measurements with the second temperature sensor; and
comparing the first and second pluralities of temperature measurements to determine whether the occlusion element is completely occluding the pulmonary vein.

11. The method of claim 10, wherein the measuring device further includes a third temperature sensor disposed within the occlusion element.

12. The method of claim 2, wherein the measured temperatures are used to predict the lesion quality during at least one of the beginning of circulation of coolant within the occlusion element and during the duration of the circulation of coolant within the occlusion element.

13. The method of claim 1, wherein the reference temperatures are compiled using empirical data from at least one of in vivo and in vitro experimentation.

14. A method for creating permanent lesions in target tissue proximate a junction between a pulmonary vein and a left atrium, the method comprising:
positioning a medical device at least partially within a pulmonary vein ostium, the medical device including a cryoballoon, a first temperature sensor disposed distal to the cryoballoon in the pulmonary vein, a second temperature sensor disposed proximal to the cryoballoon in a left atrium, and a third temperature sensor disposed within the cryoballoon, the cryoballoon being in fluid communication with a coolant source;
obtaining a first plurality of temperature measurements with the first temperature sensor and obtaining a second plurality of temperature measurements with the second temperature sensor;
comparing the first and second pluralities of temperature measurements to determine whether the cryoballoon is completely occluding the pulmonary vein;
comparing the first plurality of temperature measurements to a set of reference temperatures that correlate blood temperature to tissue temperature to provide a temperature within a thickness of a target tissue, the thickness being within which permanent lesions may be created without damage to non-target tissue; and
at least one of stopping and reducing a circulation of coolant within the cryoballoon when a determined temperature within the thickness is within ±2° C. of a temperature at which permanent lesions are formed in the target tissue.

15. The method of claim 14, wherein the measured temperatures are correlated to the reference temperatures to determine a temperature within the target tissue.

16. A system for creating permanent lesions in target tissue proximate a junction between a pulmonary vein and a left atrium, the system comprising:
a medical device including:
an occlusion element coupled to a distal end of the medical device;
a first temperature sensor coupled to the distal end of the medical device and located distal of the occlusion element;
a second temperature sensor coupled to the distal end of the medical device and located proximal of the occlusion element; and
a third temperature sensor located within the occlusion element; and
a console including:
a coolant source in fluid communication with the occlusion element; and
a computer programmed to execute an algorithm for:
comparing a first plurality of temperature measurements recorded by the first temperature sensor of blood within a pulmonary vein to a second plurality of temperature measurements recorded by the second temperature sensor of blood within a left atrium to determine whether the occlusion element is occluding a pulmonary vein ostium; and
comparing the first plurality of temperature measurements of blood within the pulmonary vein to a set of reference temperatures that correlate blood temperature to tissue temperature to provide a temperature within the target tissue.

17. The system of claim 16, wherein the computer is further programmed to execute an algorithm for calculating the thickness of the target tissue within which permanent cryoablation lesions may be created without damage to non-target tissue.

18. The system of claim 17, wherein the computer is in communication with the coolant source, the computer being further programmed to adjust a circulation of coolant within the cryoballoon when a determined temperature within the thickness is ±2° C. of a temperature at which permanent lesions form in the target tissue.

19. The system of claim 18, wherein the computer is further programmed to reduce the circulation of coolant within the cryoballoon when the determined temperature within the thickness is ±2° C. of the temperature at which permanent lesions form in the target tissue.

20. The system of claim 18, wherein the computer is further programmed to stop the circulation of coolant within the cryoballoon when the determined temperature within the thickness is ±2° C. of the temperature at which permanent lesions form in the target tissue.

21. The system of claim 16, wherein the computer is further programmed to generate an alert when a measurement of the first plurality of temperature measurements is within ±20° C. of a measurement of the second plurality of temperature measurements.

22. The system of claim 16, wherein the computer is further programmed to:
   compare the first plurality of measurements to a third plurality of temperature measurements recorded by the third temperature sensor.

\* \* \* \* \*